(12) United States Patent
Johnson et al.

(10) Patent No.: US 7,105,009 B2
(45) Date of Patent: Sep. 12, 2006

(54) ACCESS DEVICE MAINTENANCE APPARATUS AND METHOD

(75) Inventors: Gary M. Johnson, Mission Viejo, CA (US); Russell E. Ahlberg, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 671 days.

(21) Appl. No.: 10/272,568

(22) Filed: Oct. 16, 2002

(65) Prior Publication Data

US 2004/0093018 A1    May 13, 2004

(51) Int. Cl.
*A61M 25/00* (2006.01)
*A61B 17/28* (2006.01)

(52) U.S. Cl. ............... 606/205; 604/278; 604/267.03
(58) Field of Classification Search ........ 604/164–278; 606/205–207
See application file for complete search history.

(56) References Cited

U.S. PATENT DOCUMENTS

| | | | |
|---|---|---|---|
| 2,879,775 A | 3/1959 | Barr, Sr. et al. | |
| 3,994,412 A | 11/1976 | Difiglio | 220/266 |
| 4,475,548 A | 10/1984 | Muto | 128/207.14 |
| 4,863,453 A | 9/1989 | Berger et al. | 604/415 |
| 5,147,305 A | 9/1992 | Nakamura et al. | 604/110 |
| 5,197,493 A | 3/1993 | Grier-Idris | 128/853 |
| 5,429,609 A | 7/1995 | Yoon | |
| 5,460,616 A | 10/1995 | Weinstein et al. | 604/167 |
| 5,611,792 A | 3/1997 | Gustafsson | 604/403 |
| 5,720,730 A * | 2/1998 | Blake, III | 604/167.02 |
| 5,752,938 A * | 5/1998 | Flatland et al. | 604/167.01 |
| 5,989,233 A | 11/1999 | Yoon | 604/280 |
| 6,238,373 B1 * | 5/2001 | de la Torre et al. | 604/256 |

* cited by examiner

*Primary Examiner*—Vy Q. Bui
(74) *Attorney, Agent, or Firm*—Richard L. Myers; Kenneth K. Vu; David G. Majdali

(57) ABSTRACT

A trocar includes a valve housing and cannula which define a working channel. A valve disposed in the valve housing along the working channel includes a gel material which defines a slit that functions as a zero seal in the absence of an instrument, and an instrument seal in the presence of an instrument. The slit is formed by mating gel components which are preferably separated during storage of the device. This separation can be facilitated by a pull strip which can be pre-lubricated and inserted into the slit for ultimate removal prior to activation of the trocar.

24 Claims, 8 Drawing Sheets

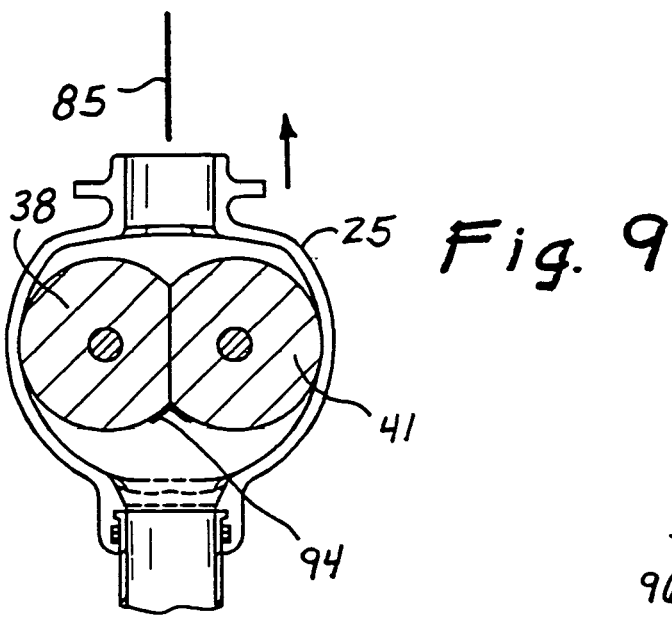
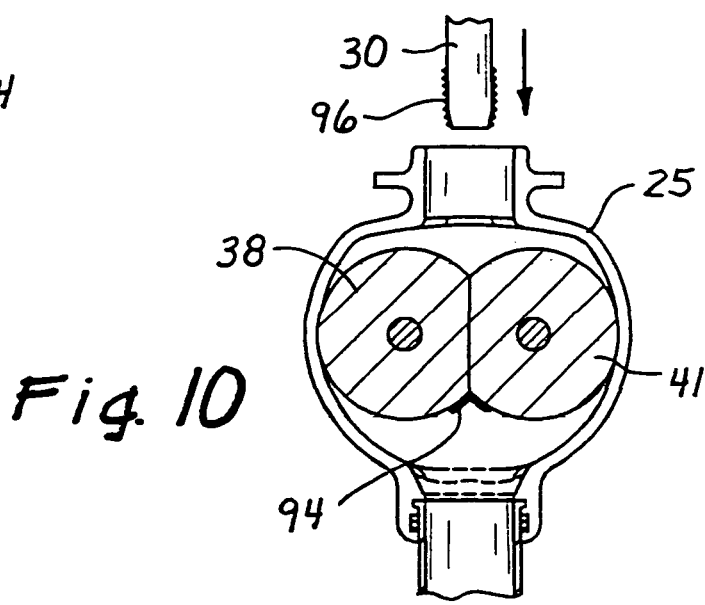
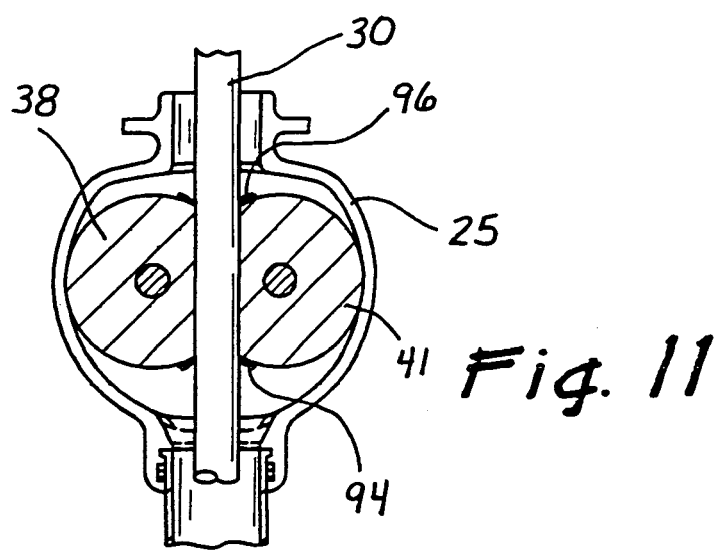

ACCESS DEVICE MAINTENANCE APPARATUS AND METHOD

BACKGROUND OF THE INVENTION

1. Field of the Invention

This invention relates generally to access devices which include compliant seal material, and more specifically to surgical access devices and methods facilitating maintenance of gel valves during periods of non-use.

2. Discussion of the Relevant Art

Access devices in general are disposed relative to a conduit and are adapted to provide input to a flow of fluid through the conduit. The device will typically is include a valve assembly which controls passage of the fluid in either a liquid state or a gas state. Such access devices may be adapted for use with fluids such as foods, oils, and grease, for example.

Devices of particular interest include surgical access devices which are commonly used to form a passageway across a body wall and into a body cavity or other body conduit. This passageway enables a surgeon operating exteriorly of the body to perform surgical operations within the body conduit by manipulating instruments through the passageway. These instruments might include, for example, scopes, needles, graspers, clamps, staplers, sutures and cutters.

Of course, the passageway, more commonly referred to as a working channel, also provides a path for fluids to exit the body from the body conduit. In order to inhibit this leakage of fluids, some access devices are provided with valves which can seal the working channel both in the absence of the instrument and in the presence of the instrument.

The sealing of the working channel is of particular importance in the case of laparoscopic surgeries where the abdominal cavity is inflated with an insufflation gas in order to distend the abdominal wall and thereby increase the size of the work environment. Trocars are commonly used as access devices for this type of surgery. The trocars include a cannula and a seal housing containing one or more valves which facilitate instrument access while inhibiting leakage of the insufflation gas.

Recently, trocar valves have been formed of highly compliant gel materials such as those disclosed and claimed by applicant in co-pending PCT Application Ser. No. PCT/US01/29682 filed on Sep. 21, 2001 and entitled "Surgical Access Apparatus and Method", which designates the United States and claims priority from U.S. patent application Ser. No. 60/241,958 filed on Oct. 19, 2000, both of which are incorporated herein by reference. The specific use of these materials as trocar valves is disclosed in PCT Application Ser. No. PCT/US02/15696, which designates the United States and claims priority from U.S. Provisional Application Ser. No. 60/312,683 filed on Aug. 14, 2001. This application, which is entitled "Access Sealing Apparatus and Method", is also incorporated herein by reference and discloses many embodiments of trocar gel valves which are all applicable to the present invention.

The gel material included in these valves may have a slight degree of cohesion which tends to degrade the function of the valve over long periods of time, such as during storage and prior to use. For example, in an embodiment including a slit formed between mating gel components, a chemical or mechanical bond can tend to form across the slit over an extended period of contact. Of course, it is desirable to inhibit this formation of bonds or otherwise to maintain or recreate the slit prior to use of the trocar.

SUMMARY OF THE INVENTION

In accordance with the present invention, a strip is inserted between the mating gel components so that they are not in contact across the slit for extended periods of time. This inhibits formation of any chemical or mechanical bonds between the gel components, particularly during long periods when the trocar is stored prior to use. The strip can be mounted in the slit using a grasper after the trocar is fully constructed. The strip can be coated so that a lubricant can be deposited on the distal side of the valve as the strip is removed from the trocar prior to use. An inserted instrument can also be coated to deposit a lubricant on the proximal side of the valve upon insertion of the instrument.

In one aspect, a medical access device has a stored state and an active state and is formed with a working channel that is adapted to provide access through the device into a body conduit. An access valve is disposed along the working channel and includes a first compliant material as well as a second material disposed in a opposing relationship with the first material. A slit is defined between the two materials, through the access valve and along the working channel. The slit, in the active state of the device, is normally closed with the first material contacting the second material. A strip disposed in the slit inhibits this contacting relationship in the stored state of the device. This strip is removable to initiate the active state.

In another aspect, the access valve is disposed along the working channel and adapted to form an instrument seal when the instrument is in the working channel. A pair of mating seal components which define the working channel through the access valve, have a tendency to form a bond when left in contact for extended periods of time. Means is provided to separate the seal components and inhibit formation of the bond when the device is not in use.

In another aspect, a method for facilitating formation of the instrument seal includes the steps of providing the access valve with a first element and a second element disposed in a normally contacting relationship. An opening between the elements extends from the proximal side to the distal side of the access valve. The first and second elements are separated to inhibit the normal contacting relationship during a period of non-use. This separation step is inhibited in order to prepare the access device for receipt of the instrument.

In another method for facilitating formation of the instrument seal, a lubrication strip is provided with a lubricant disposed in proximity to a distal end of the strip. The strip is positioned to extend between the seal components with the distal end of the strip extending distally of the distal side of the access valve. Removing the strip from between the seal components deposits the lubricant on the access valve.

In a further aspect, the separation strip can be inserted between the seal components after the access device is fully constructed. A grasper is inserted into the working channel proximally between the seal components where it engages the distal end of the strip. Then the grasper is withdrawn from the working channel pulling the strip through the working channel and between the seal components of the access device.

These and other features and advantages of the invention will become more apparent with a description of preferred embodiments and reference to the associated drawings.

DESCRIPTION OF THE DRAWINGS

FIG. 9 is an axial cross-section view similar to FIG. 7 and illustrating removal of the strip to deposit a lubricant on the access valve;

FIG. 10 is an axial cross-section view similar to FIG. 9 and illustrating a lubricated instrument inserted distally to deposit a lubricant on a proximal side of the access valve; and FIG. 11 is an axial cross-section view similar to FIG. 10 and illustrating an instrument operatively disposed between gel components with lubricant deposit on both the proximal and distal sides of the access valve.

DESCRIPTION OF PREFERRED EMBODIMENT AND BEST MODE OF THE INVENTION

Figure 1:
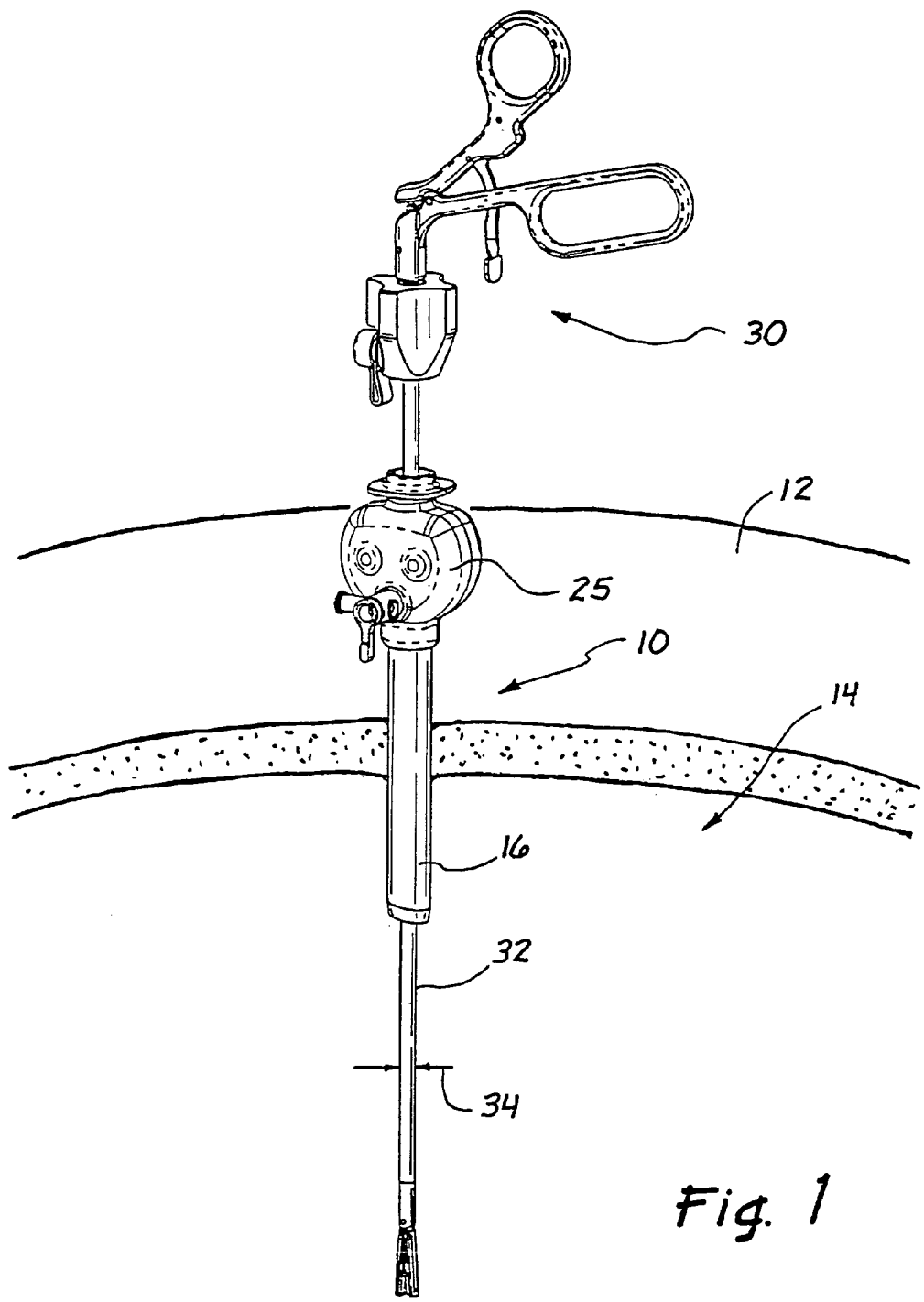
FIG. 1 is a perspective view showing a laparoscopic surgery with the surgical instrument in the form of a grasper inserted through a working channel of a trocar.
Figure 2:
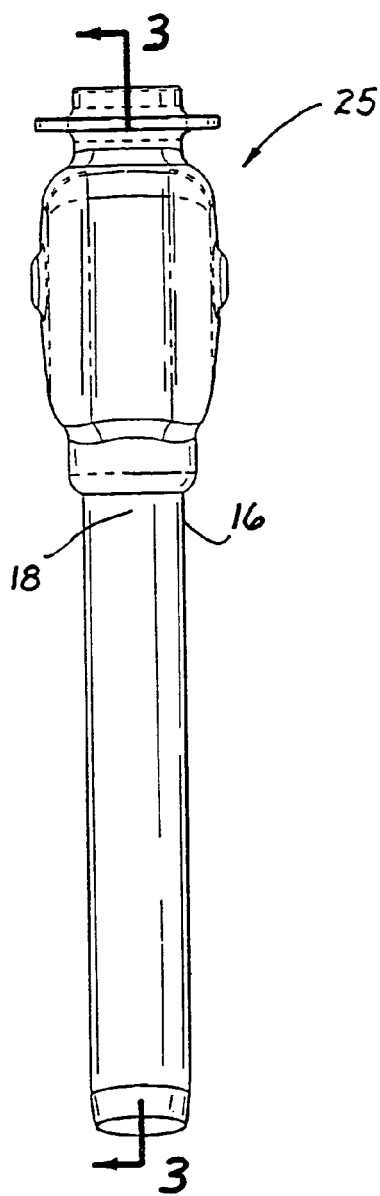
FIG. 2 is a side elevation view of the trocar illustrated in FIG. 1.

A trocar is illustrated in FIG. 1 and designated generally by the reference numeral 10. The trocar 10 exists generally in two states, a storage state prior to use, and an active state during use. In FIG. 1, the trocar 10 is illustrated in its active state, operatively disposed to provide access across a body wall, such as the abdominal wall 12, and into a cavity or other body conduit 14, such as an abdominal cavity 15. In this case, the trocar 10 is representative of any access device which extends across a body wall to provide access into a body conduit. The access device may facilitate a flow of fluids, either gas or liquid, into or out of the conduit 14; or it may accommodate a surgical instrument, such as a needle, which can be inserted through the access device and into the body conduit.

In the illustrated embodiment, the trocar 10 includes a cannula 16 which extends along an axis 18 between a proximal end 21 and a distal end 23. A seal housing 25 is disposed at the proximal end 21 of the cannula 16, and forms with the cannula 16, an access or working channel 27. This working channel 27 is sized and configured to receive a surgical instrument 30, such as a grasper, which will typically include an elongate tube or shaft 32 having a maximum dimension or diameter, shown by arrows 34.

In this case, the grasper or instrument 30 is representative of any surgical instrument or device which might be inserted through the working channel 27 of the access device on trocar 10 and into the body conduit 14. Other instruments may be as small as a suture (not shown), which might have a diameter less than one millimeter, or as large as a scope, cutter, clip applier, clamp or even a stapler, which might have a diameter more than 12 millimeters.

In general, it may be desirable that the access device, such as the trocar 10, have properties for inhibiting the egress of fluids outwardly through the working channel 27. This is particularly important in the case of laparoscopic surgeries where the abdominal cavity 15 is typically inflated with a gas in order to elevate the abdominal wall 12 and thereby increase the volume of the working environment. The sealing of the working channel 27 is of course complicated by the desire to introduce instruments, such as the grasper, along the working channel 27. Not only is sealing of the working channel 27 desired in the absence of the instrument 30, but it is also desired when the instrument 30 is operatively disposed as illustrated in FIG. 1.

Figure 3:
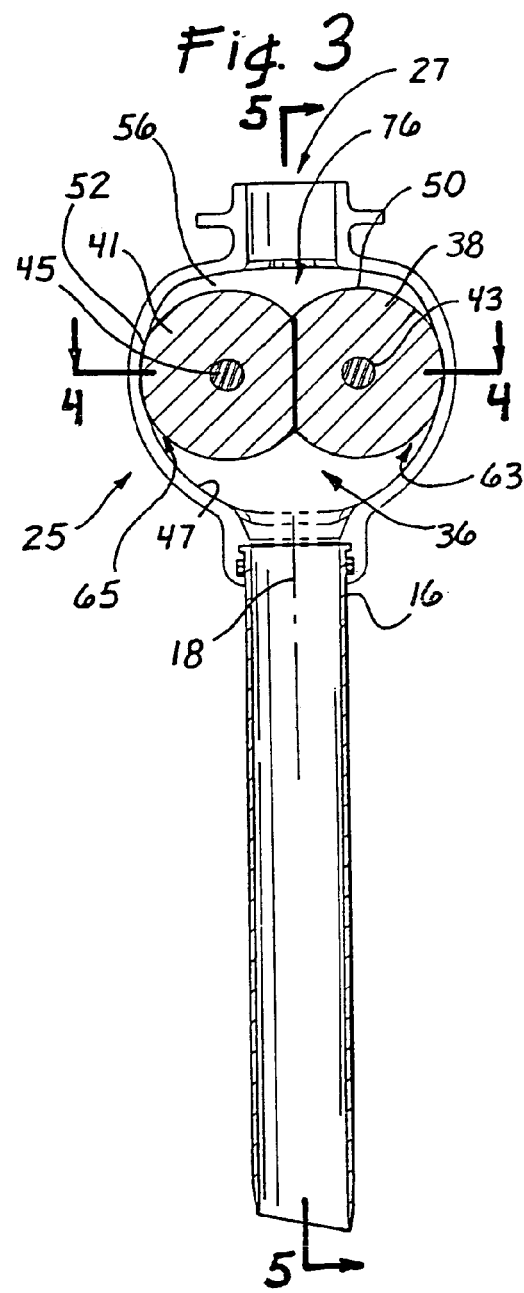
FIG. 3 is an axial cross-section view taken along lines 3—3 of FIG. 2; and illustrating interior valve components of the trocar.

A seal assembly 36 of the present invention is illustrated in the axial cross-section view of FIG. 3. This seal assembly 36 includes two mating seal components in the form of rollers 38 and 41, having axles 43 and 45, respectively. The rollers 38 and 41 are rotatable on their respective axes and relative to an inner surface 47 of the seal housing 25. The axles 43 and 45 may be rotatable with the respective rollers 38 and 41 relative to the housing 25, or may be fixed to the seal housing 25 in which case the rollers 38 and 41 also rotate relative to their respective axles 43 and 45.

Figure 4A:
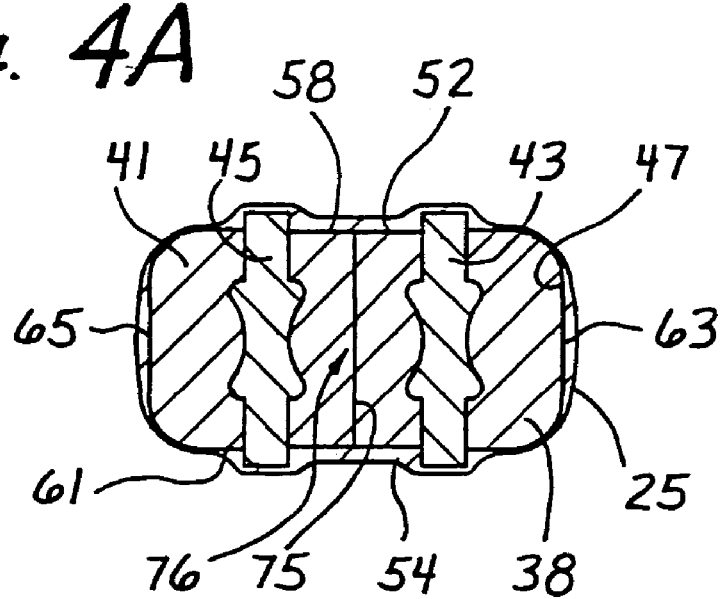
FIG. 4A is a radial cross-section view taken along lines 4—4 of FIG. 3 and illustrating the valve components in the absence of the instrument.
Figure 4B:
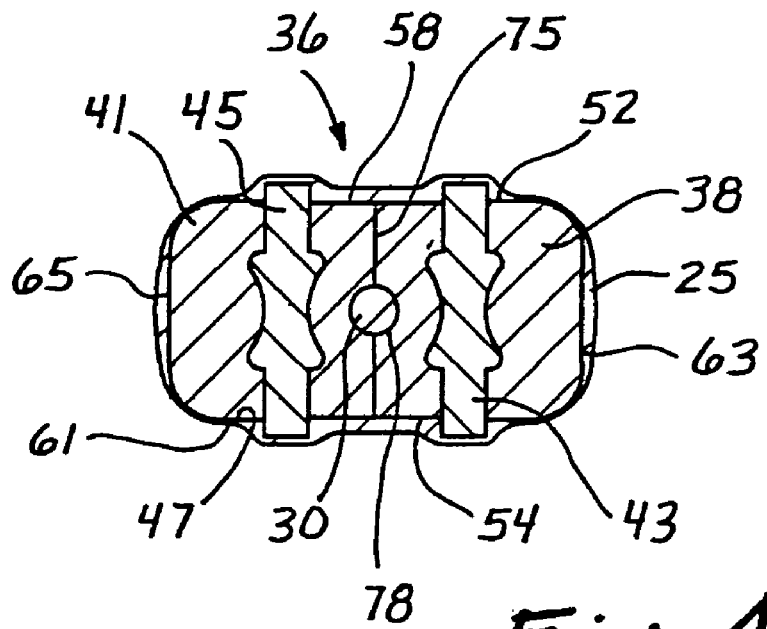
FIG. 4B is a radial cross-section view similar to FIG. 4A and illustrating the valve components in the presence of the instrument.
Figure 5:
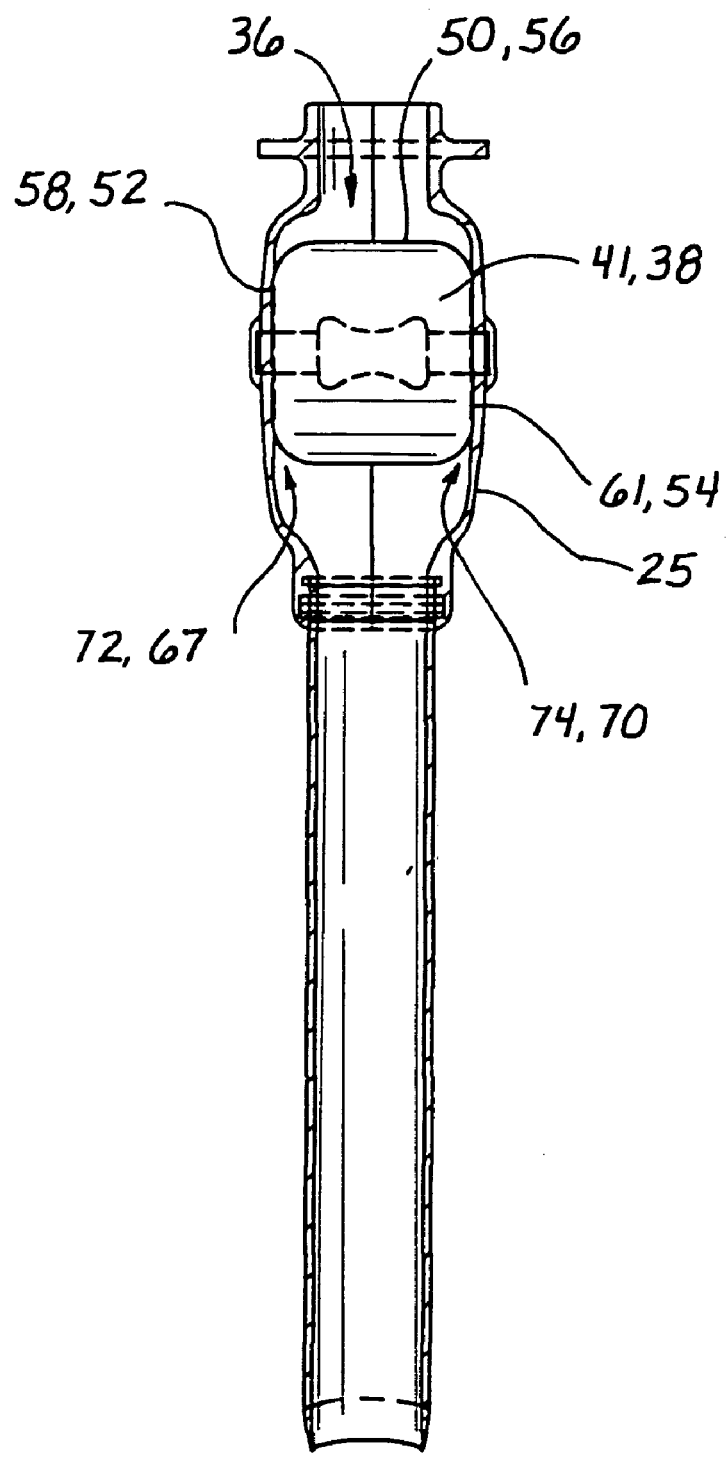
FIG. 5 is an axial-cross section view taken along lines 5—5 of FIG. 3.

In the embodiment of FIG. 3, the rollers 38 and 41 each have a cylindrical outer surface as well as a pair of end surfaces. For example, the roller 38 has a cylindrical outer surface 50 best illustrated in FIG. 3, as well as a pair of end surfaces 52 and 54, best illustrated in FIG. 4A. The roller 41 is similarly constructed with a cylindrical outer surface 56 and a pair of end surfaces 58 and 61.

In order to form the desired seals across the working channel 27, it is important that the rollers 38 and 41 form both lateral seals and end seals with the inner surface 47 of housing 25. Thus, in a preferred embodiment, lateral seals 63 and 65 are formed between the seal housing 25 and the respective cylindrical surfaces 50 and 56. Similarly, end seals are formed between the seal housing 25 and the end surfaces of each of the rollers 38 and 41. For example, end seals 67 and 70 can be formed between the seal housing 25 and the end surfaces 52 and 54 of the roller 38. Similar end seals 72 and 74 can be formed between the seal housing 25 and the end surfaces 58 and 61 of the roller 41. In combination, the lateral seals 63, 65 and the end seals 67–74 form a continuous seal between the seal assembly 36 and the seal housing 25.

Of particular importance in this embodiment is a slit 75 which is defined between the mating seal components such as the rollers 38 and 41. It is this slit 75 which is normally closed, but is openable by insertion of the surgical instrument 30 to access the body conduit 14. When the slit 75 is closed, the rollers 38 and 41 form a zero seal 76 which cooperates with the lateral seals 63–65, and the end seals 67–74 to seal the working channel 27 in the absence of the surgical instrument 30. When the instrument 30 is present in the working channel, at least portions of the slit separate to receive the instrument 30, which then forms an instrument seal 78 with the rollers 38 and 41. Thus, in the presence of the instrument 30, the instrument seal 78 cooperates with the lateral seal 63–65, and the end seal 67–74, to seal the working channel.

Given the desire to form the various seals including the lateral seals, the end seals, the zero seal, and the instrument seal, it can be appreciated that a special material is required for the rollers 38 and 41. A material of particular interest is that disclosed by applicant in co-pending application PCT/US01/29682, filed on Sep. 21, 2001, entitled "Surgical Access Apparatus and Method", and. U.S. Pat. application Ser. No. 60/241,958 filed on Oct. 19, 2000, entitled "Hand-Assisted Laparoscopy Apparatus and Method", and its counterpart which are incorporated herein by reference. This particular material is a gel material 80 which has properties including a low durometer hardness and a high tear strength. In addition, the gel material 80 tends to have flow characteristics similar to a fluid in that it is easily displaced, for example, by insertion of an instrument, without affecting the instrument seal. Although the gel has characteristics of a fluid, it also has characteristics of a solid in that it can be formed, for example, molded to a desired shape.

The trocar 10 is representative of many types of access devices which will include a seal assembly 36 with gel components. Other embodiments of such trocars in the U.S. patent applications previously mentioned and incorporated herein by reference.

Given the foregoing description of the trocar 10 in its active, in-use state, it can be appreciated that the seal assembly 36 will typically include at least two mating seal components. At least one of these components will be formed of a gel-type material as previously discussed. The other mating component may include the same material or may be formed from a different material such as plastic. In either case, the slit 75 is formed between these mating seal components.

It is certainly one of the aspects of the present invention to facilitate operation of the seal assembly 36 and particularly the slit 75 in the active state of the trocar. Notwithstanding the many advantages associated with the properties of the gel-type material, it may be desirable to separate the mating seal components of the seal assembly 36, particularly when the trocar 10 is being stored prior to use. In this stored state, a pull strip 85 can be provided for disposition between the mating seal components, such as the rollers 38 and 41. By placing the strip 85 in the slit 75, the material associated with the mating seal components can be maintained in a separate spaced relationship to inhibit any possible chemical or mechanical degradation of the slit 75.

The pull strip 85 can be manufactured from several different types of materials provided in many different forms. For example, the strip 85 may include fabric, felt, paper, waxpaper, open-cell foam, closed-cell foam, Mylar, Tyvek, (a registered trademark of Dupont) polytetrafluoroethylene, and/or nylon.

Figure 6:
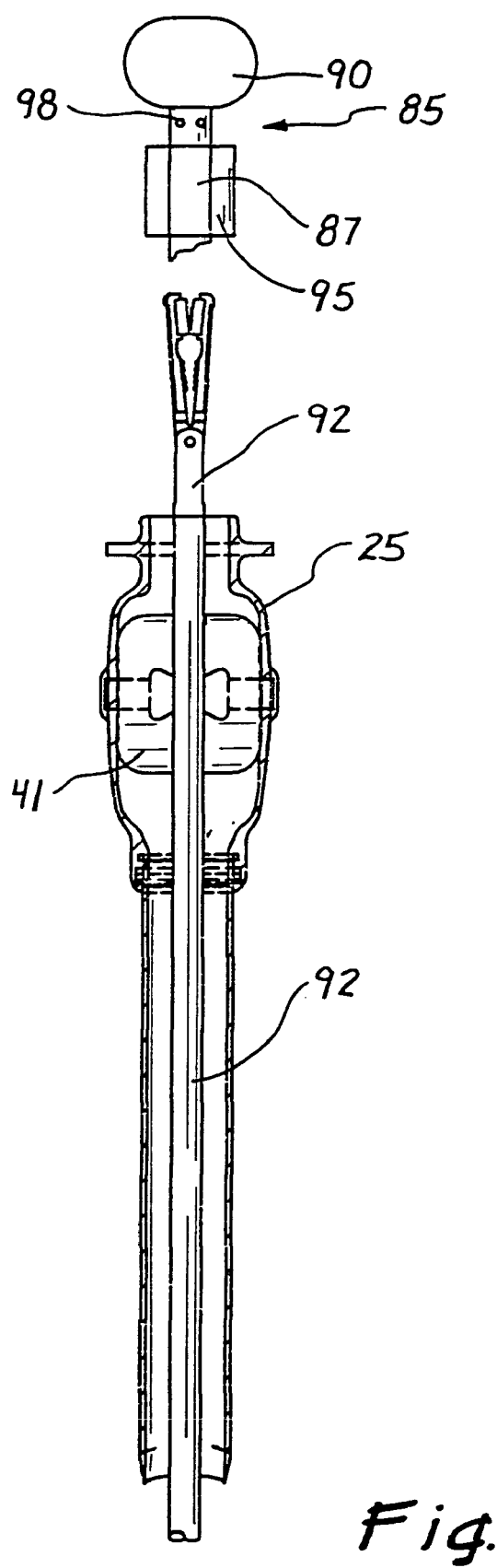
FIG. 6 is an axial cross-section view similar to FIG. 3, illustrating a preferred method of mounting a strip in a slit formed between access valve components.
Figure 7:
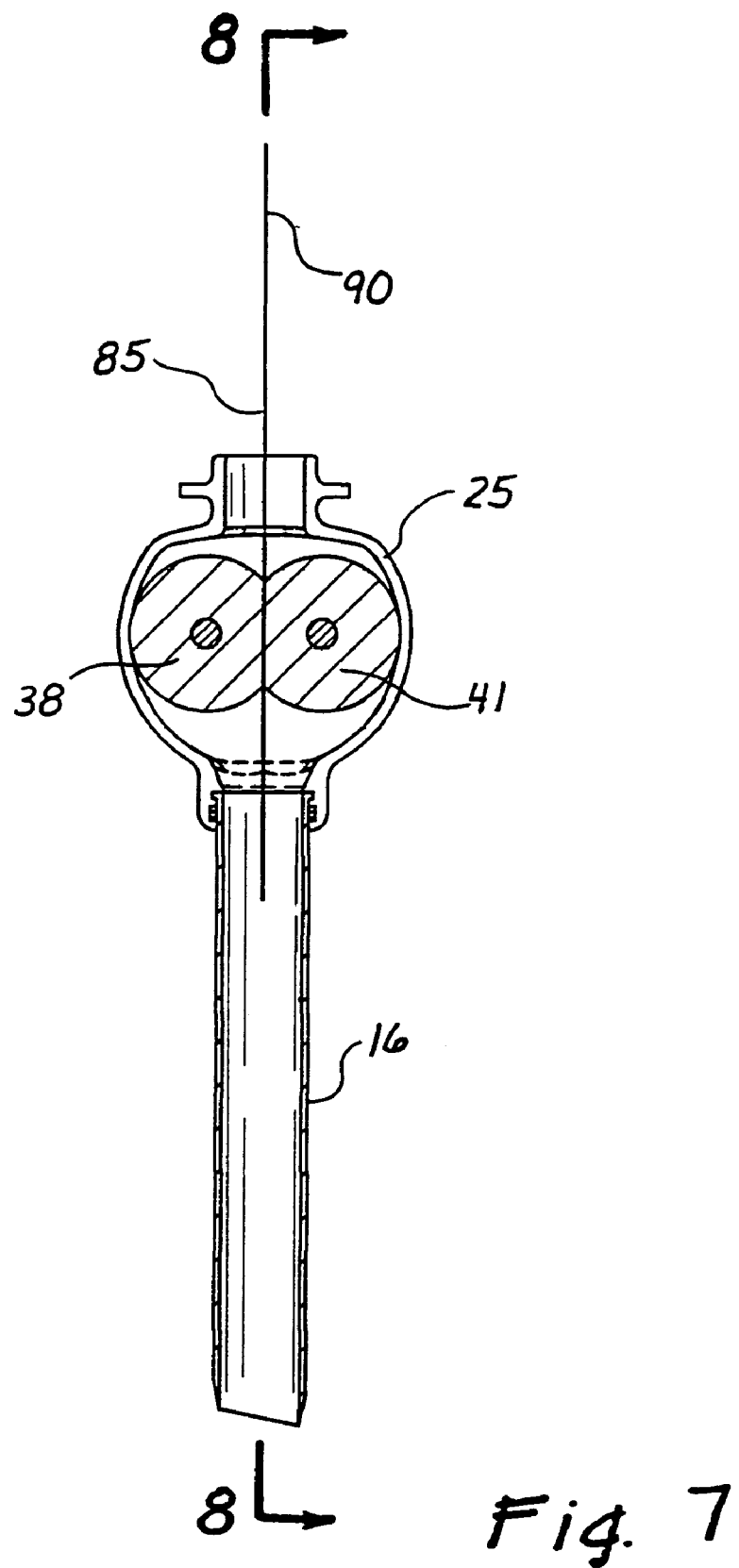
FIG. 7 is an axial cross-section view similar to FIG. 6 and illustrating the strip operatively disposed in a stored state of the device.
Figure 8:
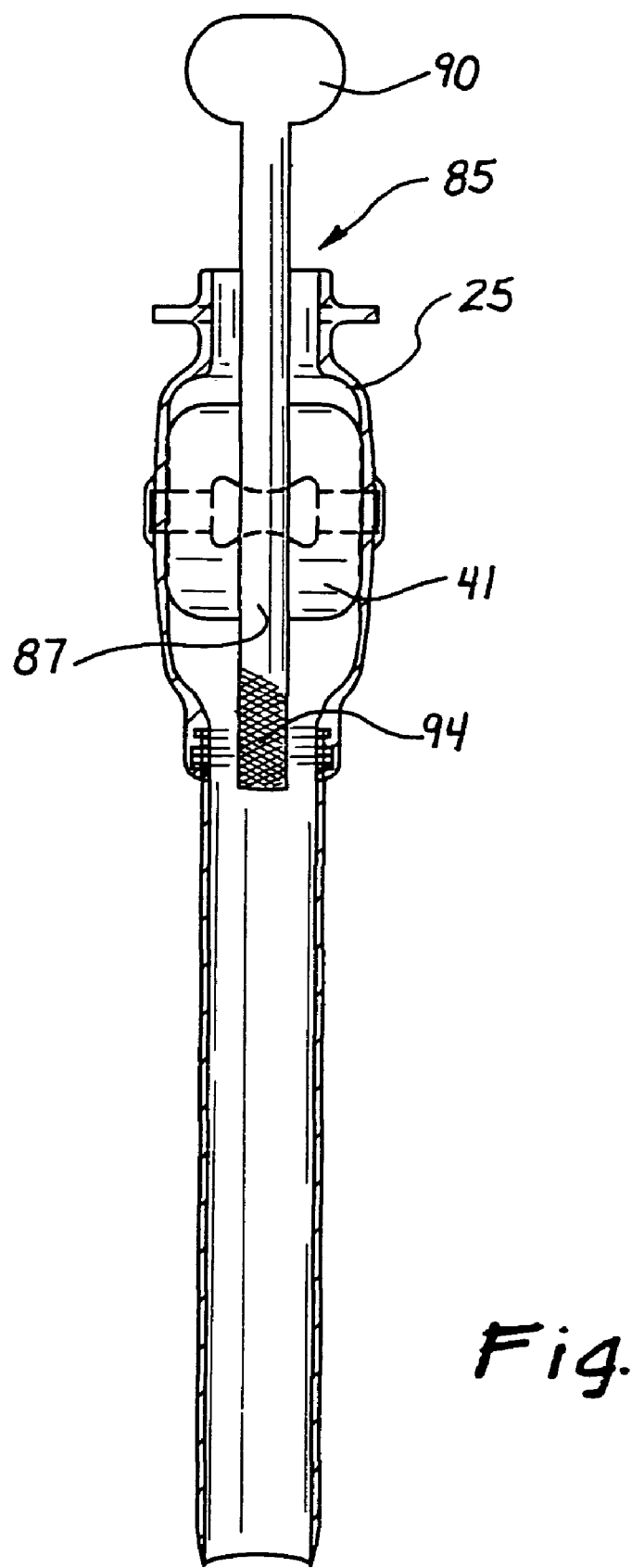
FIG. 8 is a cross-section view taken along lines 8—8 of FIG. 7

As illustrated in FIG. 6, the strip 85 may include an elongate distal portion functioning as a separator 87, and a proximal portion forming a finger tab 90. Given this configuration, the strip 85 can be loaded into the trocar as illustrated in FIG. 6. In this particular method, a grasper 92 is introduced retrograde progressively through the cannula 16, and the seal assembly 36 and the seal housing 25. At this point, the distal end or separator 87 of the strip 85 can be engaged by the grasper 92. As the grasper 92 is then progressively withdrawn from the seal housing 25 and the cannula 16, the separator 87 of the strip 85 is moved into the slit 75 between the mating seal components, such as the roller 38 and 41. This operative disposition of the strip 85 is illustrated in FIGS. 7 and 8, and characterizes the stored state of the trocar 10. With the mating seal components, such as the rollers 38 and 41 maintained in a separate, non-contacting relationship by the strip 85, the trocar 10 can be stored indefinitely awaiting removal of the strip 85 to activate the trocar 10.

With the strip 85 operatively disposed, it also provides a vehicle for lubricating the mating seal components, such as the rollers 38 and 41, immediately prior to use of the trocar 10. If a lubricant 94 is disposed on the distal end of the separator 87, this lubricant will be deposited on the mating seal components, such as the rollers 38 and 41, when the strip 85 is withdrawn proximally from the trocar 10.

There are several ways that the strip 85 can be provided with lubricant on its distal end as illustrated in FIG. 8. If the strip 85 is loaded, has not yet been moved into the slit 85, as illustrated in FIG. 6, it would appear that any lubricant on the strip 85 would be deposited on the rollers 38 and 41 as the strip 85 is moved distally through the slit 75. To inhibit this premature disposition of lubricant, it may be desirable to encase the distal end of the strip 85 and its lubricant in a sleeve 95 which maintains the lubricant 94 on the separator 87 as it passes between the rollers 38 and 41. At this point, the sleeve 95 can be removed, leaving the strip 85 operatively disposed and lubricated as illustrated in FIG. 8. If the strip 85 is not pre-lubricated, or the sleeve 95 is not used, the strip 85 can be subsequently lubricated, for example with a syringe inserted proximally through the cannula 16 or distally through the seal assembly 36. And, of course, if the strip 85 is loaded proximally through the cannula 16, any lubrication on its distal end will remain on the separator 87 distally of the rollers 38 and 41.

Another method for removably carrying the lubricant on the strip 85 would be to provide the distal end or separator 87 of the strip 85 with recesses or pockets 98 as illustrated in FIG. 6. These pockets 98 could then be filled with the lubricant 94. Several different types of materials are contemplated for the lubricants 94 and 96, including silicone oil, silicone grease, mineral oil, glycerin, water, Astroglide (a registered trademark of BioFilm, Inc.), petrolatum, and/or propylene glycol.

In order to place the trocar in its active state, the finger tab 90 can be engaged and the strip 85 moved proximally through the seal housing 25. With this proximal movement, the lubrication 94 on the distal end of the strip 85 will be drawn off on the distal side of the rollers 38 and 41, as illustrated in FIG. 9. In order to further lubricate the rollers 38 and 41, the instrument 30, prior to insertion, can be coated with a lubricant 96 and inserted distally as illustrated in FIG. 10. This will cause the lubricant 96 to be removed from the instrument 30 on the proximal side of the rollers 38, 41 as illustrated in FIG. 11. Of course in an embodiment wherein the mating seal components include one or more rollers, the gel-material will rotate, spreading the lubricants 94 and 96 along the surface of the rollers 38 and 41. Thus, immediately prior to use of the trocar 10, the strip 85 can be used to activate the trocar 10 and facilitate its impending use.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A medical access device having a stored state and an active state, and being formed with a working channel adapted to provide access through the device and into a body conduit, comprising:
an access valve disposed along the working channel;
a first compliant material included in the access valve;
a second material included in the access valve in an opposing relationship with the first material;
the first material and the second material defining a slit extending through the access valve along the working channel;
the slit in the active state of the device being normally closed with the first material contacting the second material;
a strip disposed in the slit to inhibit the contacting relationship of the first material and the second material in the stored state of the device, the strip being removable from the slit to initiate the active state.

2. The medical access device recited in claim 1, wherein the second material is a compliant material.

3. The medical access device recited in claim 2, wherein the second material is the same as the first material.

4. The medical access device recited in claim 1, wherein the strip has properties for lubricating at least one of the first material and the second material when the strip is removed from the slit.

5. The medical access device recited in claim 4, wherein the strip comprises:
a first area adapted to be disposed between the first material and the second material when the device is in the stored state;
a second area adapted to be disposed distally of the slit when the device is in the stored state; and
a lubricant carried by the second area of the strip; whereby removal of the strip proximally deposits the lubricant on at least one of the first material and the second, material.

6. The medical access device recited in claim 3, wherein the first material is a gel.

7. The medical access device recited in claim 1, wherein the strip comprises at least one of fabric, felt, paper, open-cell foam, closed-cell foam, Mylar, Tyvek, polytetrafluorethylene, and nylon.

8. A medical access device having a working channel adapted to provide access for a medical instrument into a body conduit, comprising:
an access valve disposed along the working channel and adapted to form an instrument seal with the instrument when the instrument is in the working channel;
a pair of mating seal components defining the working channel through the access valve, the seal components having a tendency to form a bond when left in contact; and
removable means for separating the seal components to inhibit formation of the bond when the device is not in use.

9. The medical access device recited in claim 8, wherein the separating means is removable from between the seal components to activate the device.

10. The medical access device recited in claim 9 wherein at least one of the seal components includes a gel.

11. The medical access device recited in claim 9, wherein the separation means comprises:

strip means for separating the seal components;
lubrication means carried by the strip means for lubricating at least one of the seal components during removal of the separation means from between the seal components.

12. The medical access device recited in claim 11, wherein the lubricating means comprises at least one of, silicone grease, mineral oil, glycerin, water, petrolatum, propylene glycol, and Astroglide, a registered trademark of BioFilm, Inc.

13. The medical access device recited in claim 11, wherein the strip means comprises at least one of fabric, felt, paper, open-cell foam, closed-cell foam, Tyvek, Mylar, polytetrafluorethylene, and nylon.

14. The medical access device recited in claim 11, wherein:
portions of the strip means define at least one reservoir; and
the lubricating means is disposed in the reservoir.

15. A method for facilitating formation of an instrument seal using a medical access device adapted to receive a medical instrument, the access device having an access valve with a proximal side and a distal side, comprising the steps of:
providing the access valve with a first element and a second element disposed in a normally contacting relationship with the first element, the second element defining with the first element a slit to receive the medical instrument, the slit extending from the proximal side of the access valve to the distal side of the access valve;
separating the first element from the second element to inhibit the normal contacting relationship of the first element and the second element during a period of non-use; and
inhibiting the separating step to prepare the access device for receipt of the instrument.

16. The method recited in claim 15, wherein the separating step includes the stop of:
occupying at least a portion of the slit with a third element in order to separate the first element from the second element.

17. The method recited in claim 16, wherein the occupying step includes the step of:
providing a strip; and
inserting the strip into the access device to extend through the slit between the proximal side and the distal side of the access device.

18. The method recited in claim 17, wherein the inhibiting step includes the step of:
removing the strip from the slit to facilitate the normal contacting relationship of the first element and the second element of the access device.

19. The method recited in claim 18, wherein the step of providing the strip includes the step of:
coating the strip with a lubricant.

20. The method recited in claim 19, wherein the step of removing the strip includes the steps of:
pulling the strip proximally from the slit; and
during the pulling strip, depositing the lubricant on at least one of the first element and the second element of the access device.

21. A method for facilitating formation of an instrument seal using a medical access device adapted to receive a medical instrument, comprising the steps of:
providing an access valve having a pair of complimenting seal components defining a proximal side and a distal side of the access valve, the seal components being adapted to form the instrument seal with the instrument;

providing a lubrication strip with a lubricant disposed in proximity to a distal end of the strip;

positioning the lubricating strip to extend between the seal components with the distal end of the strip extending distally of the distal side of the access valve;

removing the strip from between the seal components; and during the removing step depositing the lubricant on the access valve.

22. The method recited in claim 21, further comprising the steps of:

inserting the instrument between the seal components to form the instrument seal.

23. The method recited in claim 22, wherein the lubricant is a first lubricant and the method further comprises the step of:

coating the instrument with a second lubricant; and during the inserting step depositing the second lubricant on the access valve.

24. The method recited in claim 23, wherein:

the removing step includes the step of depositing the first lubricant on the distal side of the access valve; and the inserting step includes the step of depositing the second lubricant on the proximal side of the access valve.

* * * * *